US012144599B2

(12) United States Patent
Grabovoi (10) Patent No.: US 12,144,599 B2
(45) Date of Patent: Nov. 19, 2024

(54) DEVICE OF DEVELOPMENT OF CONCENTRATIONS OF ETERNAL LIFE PRK-1U IS OF THREE-MODES

(71) Applicant: Grigorii Petrovich Grabovoi, Belgrade (RS)

(72) Inventor: Grigorii Petrovich Grabovoi, Belgrade (RS)

( * ) Notice: Subject to any disclaimer, the term of this patent is extended or adjusted under 35 U.S.C. 154(b) by 718 days.

(21) Appl. No.: 16/504,293

(22) Filed: Jul. 7, 2019

(65) Prior Publication Data
US 2020/0008700 A1 Jan. 9, 2020

Related U.S. Application Data

(60) Provisional application No. 62/695,756, filed on Jul. 9, 2018.

(51) Int. Cl.
*A61B 5/05* (2021.01)
*A61B 5/00* (2006.01)
*A61M 21/00* (2006.01)
*G09B 19/00* (2006.01)

(52) U.S. Cl.
CPC .............. *A61B 5/05* (2013.01); *A61B 5/0059* (2013.01); *G09B 19/00* (2013.01); *A61M 21/00* (2013.01)

(58) Field of Classification Search
CPC ... A61B 5/05–055; A61B 5/168; A61B 5/486; A61B 5/4064; A61B 5/4854; A61B 5/242; A61M 21/00–02; A61M 2205/3303–3306; A61M 2205/583; A61M 2230/00
See application file for complete search history.

*Primary Examiner* — Thaddeus B Cox
(74) *Attorney, Agent, or Firm* — Georgiy L. Khayet (57) ABSTRACT

Devices and methods for development of concentration are described herein. A three-mode device for development of concentration may include an optical sensing unit. The optical sensing unit may include a plurality of sensitive elements configured to sense a signal provided by a user. The signal may be associated with a plurality of electromagnetic fields. The plurality of sensitive elements may be configured to impose the plurality of electromagnetic fields onto each other to obtain an outgoing signal. The device may further include an optical emitting unit configured to emit the outgoing signal and one or more lenses for focusing concentration of the user. The one or more lenses may be associated with the optical sensing unit. The device may further include two switches for switching between a plurality of operation modes and a lighting unit to indicate each of the plurality of operation modes by emitting a predetermined light signal.

15 Claims, 10 Drawing Sheets

DEVICE OF DEVELOPMENT OF CONCENTRATIONS OF ETERNAL LIFE PRK-1U IS OF THREE-MODES

CROSS-REFERENCE TO RELATED APPLICATIONS

This application claims priority of U.S. Provisional Patent Application No. 62/695,756 filed on Jul. 9, 2018, entitled "DEVICE OF DEVELOPMENT OF CONCENTRATIONS OF ETERNAL LIFE PRK-1U IS OF THREE-MODES," which is incorporated herein by reference in its entirety.

TECHNICAL FIELD

The present disclosure relates generally to optical devices and, more specifically, to a device for developing concentration.

BACKGROUND

The approaches described in this section could be pursued but are not necessarily approaches that have previously been conceived or pursued. Therefore, unless otherwise indicated, it should not be assumed that any of the approaches described in this section qualify as prior art merely by virtue of their inclusion in this section.

The variety of devices for sensing and/or determining physical and physiological parameters of a human body increases rapidly. However, the list of vital signs that may be sensed by such devices is mostly limited to a heart rate, blood pressure, blood oxygen level, blood sugar level, body temperature, and some other parameters. Meanwhile, it is generally known that cells of a human body, e.g., neurons, produce electrical activity. In particular, nerve impulses generated by neurons are electrical signals that create electromagnetic fields of the human body. Furthermore, some fluids of the human body are known to act as electrolytes and the flow of such fluids may generate fluctuating electromagnetic fields in the human body. However, conventional electromagnetic sensors are not intended for detecting the electromagnetic fields of the human body and are unable to transform electromagnetic signals emitted by the human body.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Provided are devices and methods for development of concentration. In some example embodiments, a three-mode device for development of concentration may include an optical sensing unit. The optical sensing unit may include a plurality of sensitive elements. The plurality of sensitive elements may be configured to sense, in one or more of a plurality of operation modes, a signal provided by a user. The signal may be associated with a plurality of electromagnetic fields. The plurality of sensitive elements may be configured to impose, based on the signal, the plurality of electromagnetic fields onto each other to obtain an outgoing signal. The three-mode device for development of concentration may further include an optical emitting unit configured to emit the outgoing signal and one or more lenses for focusing concentration of the user. The one or more lenses may be associated with the optical sensing unit. The three-mode device for development of concentration may further include two switches for switching between the plurality of operation modes and a lighting unit to indicate each of the plurality of operation modes by emitting a predetermined light signal.

A method for development of concentration may commence with providing one or more lenses for focusing the concentration of a user. The one or more lenses may be associated with an optical sensing unit. The method may further include switching between a plurality of operation modes using two switches and indicating, by a lighting unit, each of the plurality of operation modes by emitting a predetermined light signal. The method may continue with sensing, by a plurality of sensitive elements of the optical sensing unit, in one or more of the plurality of operation modes, a signal provided by the user. The signal may be associated with a plurality of electromagnetic fields. The method may continue with imposing, by the optical sensing unit, based on the signal, the plurality of electromagnetic fields onto each other to obtain an outgoing signal. The method may further include emitting, by an optical emitting unit, the outgoing signal.

Additional objects, advantages, and novel features will be set forth in part in the detailed description section of this disclosure, which follows, and in part will become apparent to those skilled in the art upon examination of this specification and the accompanying drawings or may be learned by production or operation of the example embodiments. The objects and advantages of the concepts may be realized and attained by means of the methodologies, instrumentalities, and combinations particularly pointed out in the appended claims.

BRIEF DESCRIPTION OF THE DRAWINGS

Embodiments are illustrated by way of example and not limitation in the figures of the accompanying drawings, in which like references indicate similar elements and in which.

DETAILED DESCRIPTION

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical, and electrical changes can be made without departing from the scope of what is claimed. The following detailed description is, therefore, not to be taken in a limiting sense, and the scope is defined by the appended claims and their equivalents. In this document, the terms "a" and "an" are used, as is common in patent documents, to include one or more than one. In this document, the term "or" is used to refer to a nonexclusive "or," such that "A or B" includes "A but not B," "B but not A," and "A and B," unless otherwise indicated.

The present disclosure relates to methods and devices for development of concentration. Specifically, the development of concentration is provided by a three-mode device for development of concentration, also referred herein to as a three-mode device PRK-1U for development of concentration. The device may include an optical sensing unit configured to sense signals emitted by a user and an optical emitting unit configured to emit an outgoing signal. The device further includes lenses for focusing concentration of the user, switches for switching between operation modes, and a lighting unit to indicate a current operation mode by emitting a predetermined light signal. The device may further have one or more plates with numerical symbols for focusing the concentration of the user.

The device may include a housing in which elements of the device may be located. The housing may have a parallelepiped shape. The housing may be provided with a cover placed onto the housing to enclose the elements of the device inside the housing. The lenses and plates with numerical symbols for focusing concentration may be attached to an outer surface of the housing or to the cover. The user may be located in proximity to the device. The development of concentration of the user may be provided by focusing user attention on a receiver of the device and controlling the results of the concentration. The lenses and/or the plates with numerical symbols may be configured to be the receiver of concentration of the user. To initiate development of concentration, the user may start concentrating on the lenses and/or the numerical symbols provided on the plates attached to the housing or the cover. Specifically, the user may focus user attention on the lenses and/or the numerical symbols and direct thoughts to the lenses and/or the numerical symbols of the device. The concentration of the user may include thoughts related to providing an eternal life, including concentration on being healthy, concentration on having the quality of control forecasting or control foresight, concentration on rejuvenation, concentration on a particular event in life, and so forth.

As known in psychology, the stronger a person concentrates on a goal, the events in the person's life are optimized and the goal is achieved faster. When concentrating, the user may perform the following actions. The user may imagine user consciousness as a sphere around the user's body informationally supported by the user's body itself. The further action of the user may include imagining that the sphere transforms into a shape similar to the shape of the user's body and then superimposes the shape onto the surface of the user's body. At the moment of superimposing, the user may imagine that the inner surface of the body-like shape comes into contact with the surface of the user's body and that the radiation from the outer's surface of this body-like shape spreads to all external infinite space relative to the user's body. The infinite space is considered to be the eternal reality connected with the organism of the user, which results in development of concentration on eternal life.

The devices and methods described herein are based on the principle of similarity. The principle of similarity is based on the theory of wave synthesis in combination with the unified reality theory (see Ph.D. Thesis in Physical and Mathematical Sciences, G. P. Grabovoi, "Research and Analysis of Fundamental Definitions of Optical Systems for Prediction of Industrial Nature Earthquakes and Disasters", Moscow, RAEN Publishing House, 1999, pp. 9-19; patent of the inventor No. RU 2148845C1 titled "Method of Prevention of Catastrophes and Equipment for its Realization"; and patent of the inventor No. RU 2163419C1 titled "Data Transmission System," which are incorporated herein by reference in their entirety). The devices and methods are further based on physical and mathematical theory, experimental results, physical and mathematical calculations, and the results of these calculations set forth in the publication titled "Research and Analysis of the Fundamental Definitions of Optical Systems in Disaster Prevention and Predictive Microprocessor Control", "Electronic Equipment, Series 3, Microelectronics", 1999, edition 1 (153), and other scientific materials.

In accordance with the wave synthesis theory, reality can be considered as a periodic intersection of stationary regions with dynamic regions, while in the intersection zones a synthesis of a dynamic wave and a stationary wave occurs. Any reality phenomenon can be defined in a form of optical systems. Human perception is performed using image-bearing elements of light that contain information. In case of transmitting information from a person generating information to be transmitted to an optical sensing element, the person may be considered to be a transmitting optical system. The transmitted information generated by thoughts of the person is received by an optical sensing unit to which the person directs the generated thought. As a thought is an electromagnetic wave, it can be transmitted as an element of an optical system. Sensitive elements of the optical sensing unit preferably have the shape of a sphere, as the spherical shape of the sensitive element provides the maximum activation of the sensitive element due to internal reflection of signals. The collection of trial records and testimonies of use of the three-mode device PRK-1U for the development of the concentration is presented in the Appendix of Specification.

The three-mode device for development of concentration performs the imposition of fields from the generation of biological signals and electromagnetic fields (electromagnetic waves generated by the user) according to the principle of universal connection with control of the purpose of concentration. The device further develops concentration of creational control.

In the wave synthesis theory, it is known that a thought generated in a form of radiation simultaneously has two quantum states. The first state is located on a sensing element of a signal transmitter, and the second state is located on a signal receiver. Based on these principles, the device for interacting with thoughts to develop the concentration as described herein was created.

Figure 1:
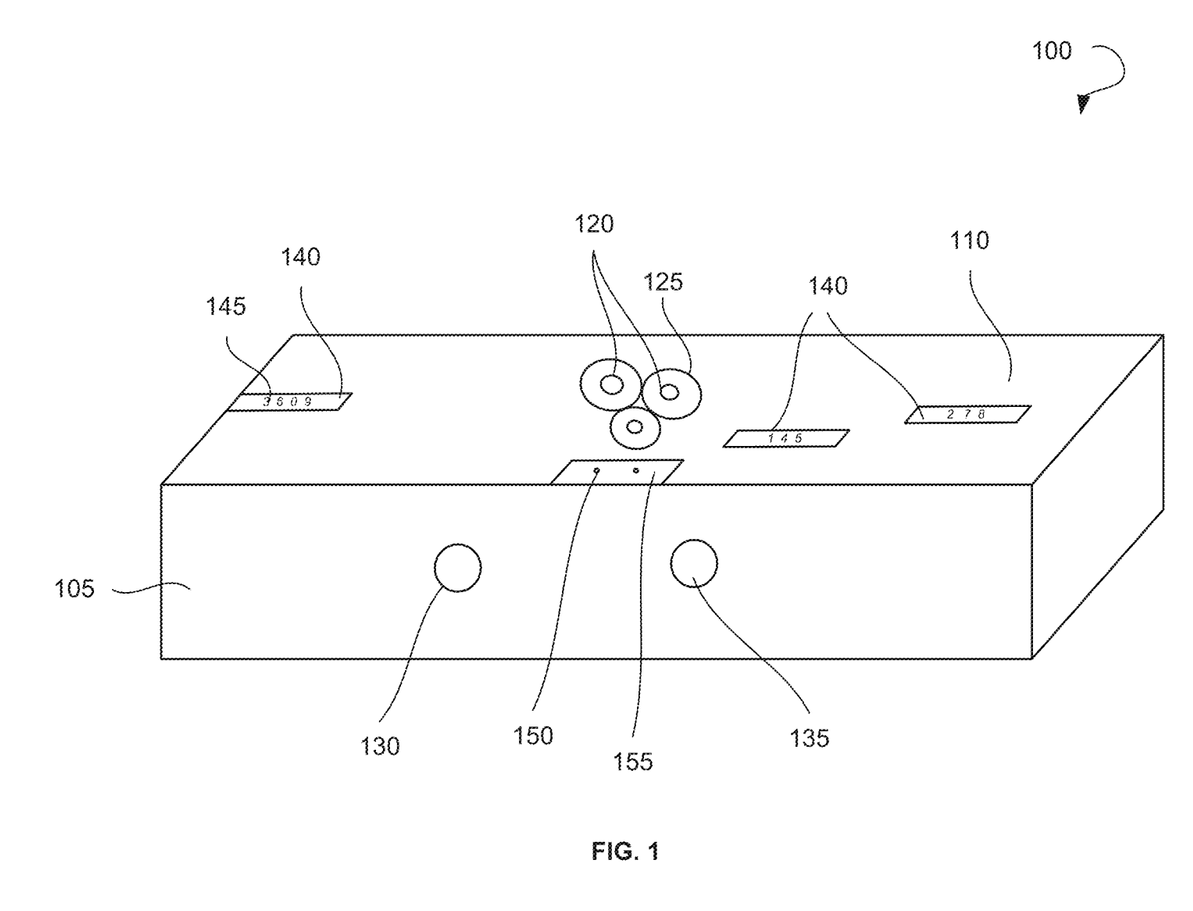
FIG. 1 illustrates a general perspective view of a three-mode device for development of concentration, in accordance with an example embodiment.

Referring now to the drawings, FIG. 1 is a general perspective view of a three-mode device 100 for development of concentration, hereinafter referred to as a device 100. The device 100 may include a housing 105 and a cover 110. In an example embodiment, the housing 100 may include a box of a rectangular shape. The device 100 may further include lenses 120. The lenses 120 may be attached to an outer surface of the cover 110. In an example embodiment, the lenses 120 may be made of glass. Each of the lenses 120 may be placed on a plate 125 (e.g., a metal plate). The diameter of the lenses 120 may be 20 mm, 25 mm, 60 mm, and any other diameter applicable for a particular embodiment of the device 100. The diameter of the plate 125 may be 60 mm, 64 mm, 70 mm, and any other diameter applicable for a particular embodiment of the device 100.

The device may further have a first switch 130 and a second switch 135 to switch between operation modes of the device 100. The device 100 may have one or more plates 140 with numerical symbols 145 depicted on the plates 140. The device 100 may further have one or more stones 150, such as diamonds, attached to the housing 105 or the cover 110 of the device 100. The stones may be placed on a plate 155. Further elements of the device 100 are shown in detail with reference to FIGS. 2-9.

Figure 2:
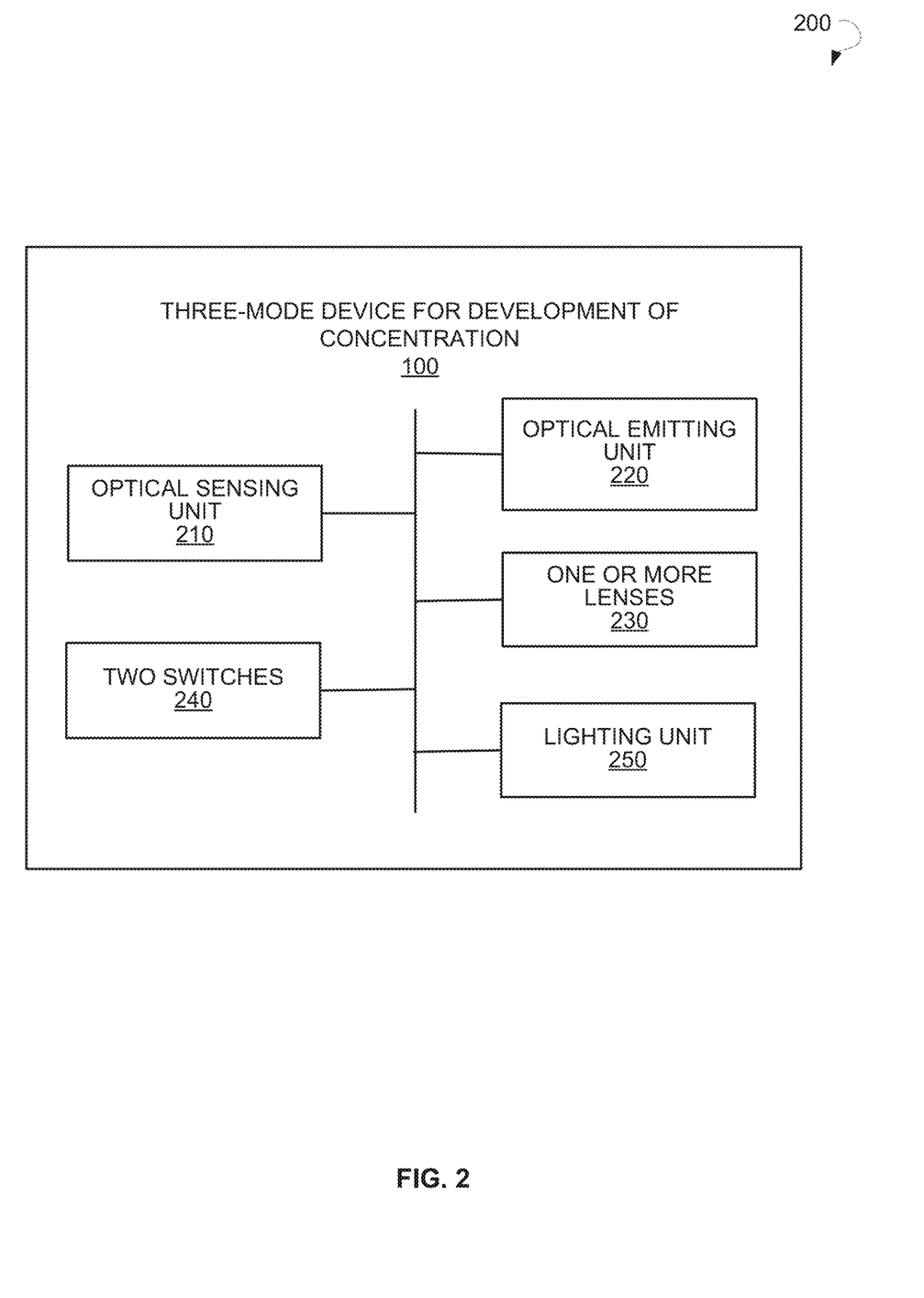
FIG. 2 is a block diagram showing various modules of a three-mode device for development of concentration, in accordance with an example embodiment.

FIG. 2 is a block diagram showing various units of a three-mode device 100 for development of concentration, in accordance with certain embodiments. Specifically, the device 100 may include an optical sensing unit 210, optical emitting unit 220, one or more lenses 230, two switches 240, and a lighting unit 250. The one or more lenses 230 for focusing concentration of a user may be associated with the optical sensing unit 210. The device 100 may further include a housing and a cover. The one or more lenses 230 may be disposed on the cover.

The optical sensing unit 210 may have a plurality of sensitive elements. In an example embodiment, the plurality of sensitive elements may be spherical. In an example embodiment, the sensitive elements may be made of glass. The plurality of sensitive elements may be configured to sense a signal provided by the user. The sensitive elements may sense the signal in one or more of a plurality of operation modes of the device 100. The signal may be associated with a plurality of electromagnetic fields. The signal provided by the user may be a biological signal. The biological signal may include an electromagnetic wave associated with thoughts generated by the user when concentrating on the one or more lenses 230 for focusing concentration. Specifically, the information (signal) may be generated in a form of electromagnetic radiation by the user. The user concentrates the electromagnetic radiation created by thought on the one or more lenses 230 located on the upper surface of the device 100.

The plurality of sensitive elements may be further configured to impose, based on the signal, the plurality of electromagnetic fields onto each other to obtain an outgoing signal. The optical emitting unit may be configured to emit the outgoing signal. In an example embodiment, the optical emitting unit 220 may include an optical lens. In an example embodiment, the optical lens may be made of glass. The optical emitting unit 220 may emit the outgoing signal in a form of at least an optical signal. In an example embodiment, the device 100 may include a further plurality of sensitive elements. The further plurality of sensitive elements may include crystals and stones, such as diamonds.

The two switches 240 may be used for switching between the plurality of operation modes of the device 100. The lighting unit 250 may be configured to indicate each of the plurality of operation modes of the device 100 by emitting a predetermined light signal. Specifically, the plurality of operation modes may include at least three modes. A first operation mode may be turned on by moving a first switch of the two switches 240 into an upward position. The first operation mode may be characterized by absence of emittance of a light signal by the lighting unit 250. A second operation mode may be turned on by moving a second switch of the two switches into an upward position. The second operation mode may be characterized by emittance of a static light signal by the lighting unit 250. A third operation mode may be turned on by moving the first switch into a downward position and further moving the first switch into an upward position while the second switch remains in the upward position. The third operation mode may be characterized by emittance of a repetitively-pulsed light signal by the lighting unit 250.

In an example embodiment, the two switches 240 may be made of a transparent or semi-transparent material, such as glass or plastics. The device 100 may have a light emitting diode (LED) disposed inside the housing for emitting the light signal. When the LED emits light inside the device 100, the light emitted from inside of the device 100 can be seen through the two switches 240. Upon switching between the operation modes, the LED may not emit light, may continuously emit light (i.e., provide the static light signal), and may repetitively emit light (i.e., provide the repetitively-pulsed light signal).

The signal provided by the user may be sensed in each of the operation modes. For example, the device 100 may be switched to the second operation mode and the optical sensing unit 210 may sense the signal provided by the user when the device 100 operates in the second operation mode. In an example embodiment, the device 100 may be switched to the third operation mode and the optical sensing unit 210 may sense the signal provided by the user when the device 100 operates in the third operation mode. The operation modes of the device 100 may be used to increase the concentration on the user.

In an example embodiment, the device 100 may further include a plurality of figures placed on the housing and/or the cover of the device 100. The figures may include numerical symbols for focusing the concentration of the user. The numerical symbols may be depicted on plates (e.g., metal, plastics, paper, wooden plates, etc.), which can be attached to the housing and/or the cover of the device 100.

The numerical symbols depicted on the plates may be used for focusing the concentration of the user.

In an example embodiment, the device 100 may further include a converting unit configured to convert the outgoing signal into an electrical signal. In an example embodiment, the converting unit may be connected to a processing unit. The processing unit may be in communication with the optical sensing unit 210, the optical emitting unit 220, and the lighting unit 250 and perform processing of sensed signals, imposed signals, optical signals, and outgoing signals. The device 100 may further include a power source in communication with the optical sensing unit 210, the optical emitting unit 220, and the lighting unit 250.

In the publication titled "Research and Analysis of the Fundamental Definitions of Optical Systems in Disaster Prevention and Predictive Microprocessor Control," "Electronic Equipment, Series 3, Microelectronics,", 1999, edition 1 (153), the inventor proves the unified reality theory and the theory of wave synthesis. According to the unified reality theory and the theory of wave synthesis, the second operation mode results in applying the amplification of the stationary phase of the reality. Furthermore, according to the unified reality theory and the theory of wave synthesis, the third operation mode results in applying the amplification of the dynamic phase of reality.

The technique of providing eternal life can work according to the principle similar to principles of functioning of the human body in the field of thinking. According to the principle of functioning of the human body when creating thoughts, the physical body of a person consists of the same tissues that do not change in the process of thinking, but thoughts that are created in the physical body are different. In the three-mode device 100 for development of concentration, the similarity principle is applied, which is illustrated by the fact that the same two buttons (i.e., switches) are used to activate the third operation mode for amplification of the dynamic phase of the reality. In other words, no elements are added to the device 100 just as no elements are added to the human body when a new thought is created. The third operation mode is turned on by turning the first switch off and on (to the downward and upward position) again while the second switch remains in the upward position. Therefore, switching between three operation modes may be provided by two switches.

Thus, by using the unified reality theory and the theory of wave synthesis proved by physical and mathematical calculations and experiments, the components are selected and an electrical scheme is developed for the device 100 so that the device 100 is similar to a human body in the following sense. A human body generates thoughts without adding any matter (components) to the human body. Similarly, the device 100 autonomously, without adding further switches, i.e., in a closed system, generates the third operation mode for amplification of the dynamic phase of the reality, which is illustrated by the repetitively-pulsed light emittance. In other words, the element base of the device 100 has a self-development function similar to that in the human body. This function of the device 100, due to the interaction of the components of the device 100, itself includes the activation of the operation mode for repetitively-pulsed light emittance. This allows the development of concentration when using the device 100, as the preceding level of developing the concentration, including that achieved with the help of the device 100 itself, is always the starting point for further development of concentration.

The work with the device 100 in different operation modes provides extensive results on the development of concentration, which is required in many areas of life, including production, operational activity, and other activities in industrial fields.

The device 100 may further be configured to activate an artificial intelligence function. This function enables the device 100, depending on the activity of generation of thoughts by the user and depending on the degree of development of concentration on eternal life in respect to specific events, to independently switch off the operation modes of the device 100 and then, after a time period determined by the device 100, again switch on any of three operation modes. Accordingly, the procedure of activation of this artificial intelligence function was developed.

The device 100 provides the capability to combine three modes of operation, thereby creating better concentration on ensuring eternal life.

Figure 3:
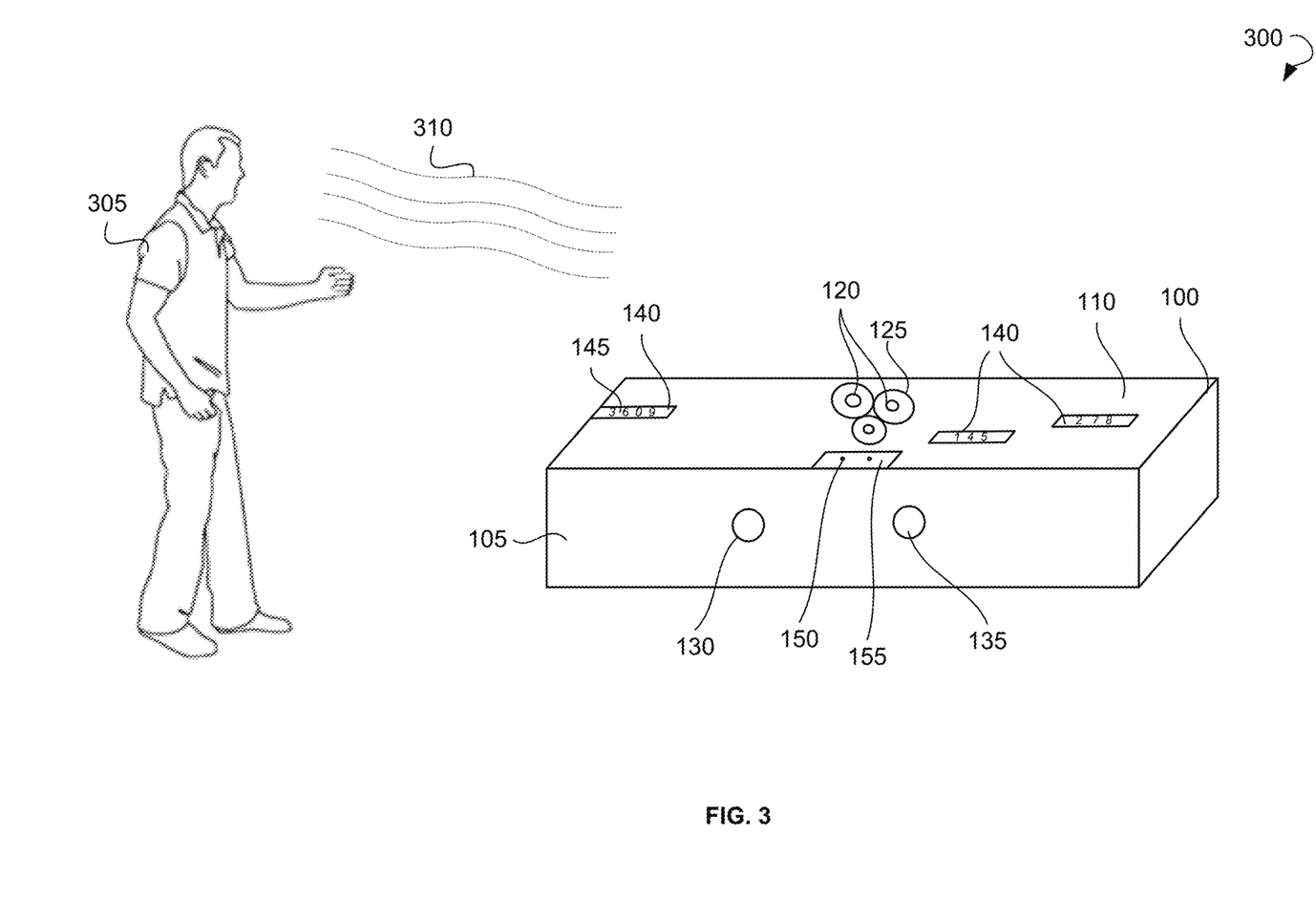
FIG. 3 is a schematic diagram illustrating development of concentration of a user using a three-mode device for development of concentration, in accordance with an example embodiment.

FIG. 3 is a schematic diagram 300 illustrating development of concentration of a user using a three-mode device 100 for development of concentration, according to an example embodiment. A user 305 may be located in a proximity of the device 100. The user 305 may concentrate user attention on lenses 120 and/or numerical figures 145 of the device 100. The lenses 120 may have different diameters. By concentrating, the user 305 generates thoughts, which are electromagnetic signals 310. The thoughts may contain the purpose of concentration, such as concentration on eternal life, concentration on being healthy, concentration on having the quality of control forecasting or control foresight, concentration on rejuvenation, and so forth. The action of concentration for the current time and future time may be performed with respect to a sensing element of the optical emitting unit consisting of lenses. The user 305 may perform circular movements associated with the concentration (i.e., direct thoughts) by following a direction from a lens of a smaller diameter counterclockwise to lenses of a larger diameter. In the case of concentrations related to the current time and future time, a concentration beam may be directed in a direction from outside of the device 100 to an inner space of the device 100.

If the concentration of the user 305 relates to past events, the user 305 may perform circular movements associated with the concentration by following a direction from a lens of a smaller diameter clockwise to lenses of a larger diameter. The concentration beam may be directed in a direction from inside the device 100 to an outside space.

In accordance with the information transmission on the basis of the wave synthesis theory, another quantum state of thoughts may be projected on a signal receiver in a form of an optical emitting unit located inside the device 100.

Figure 4:
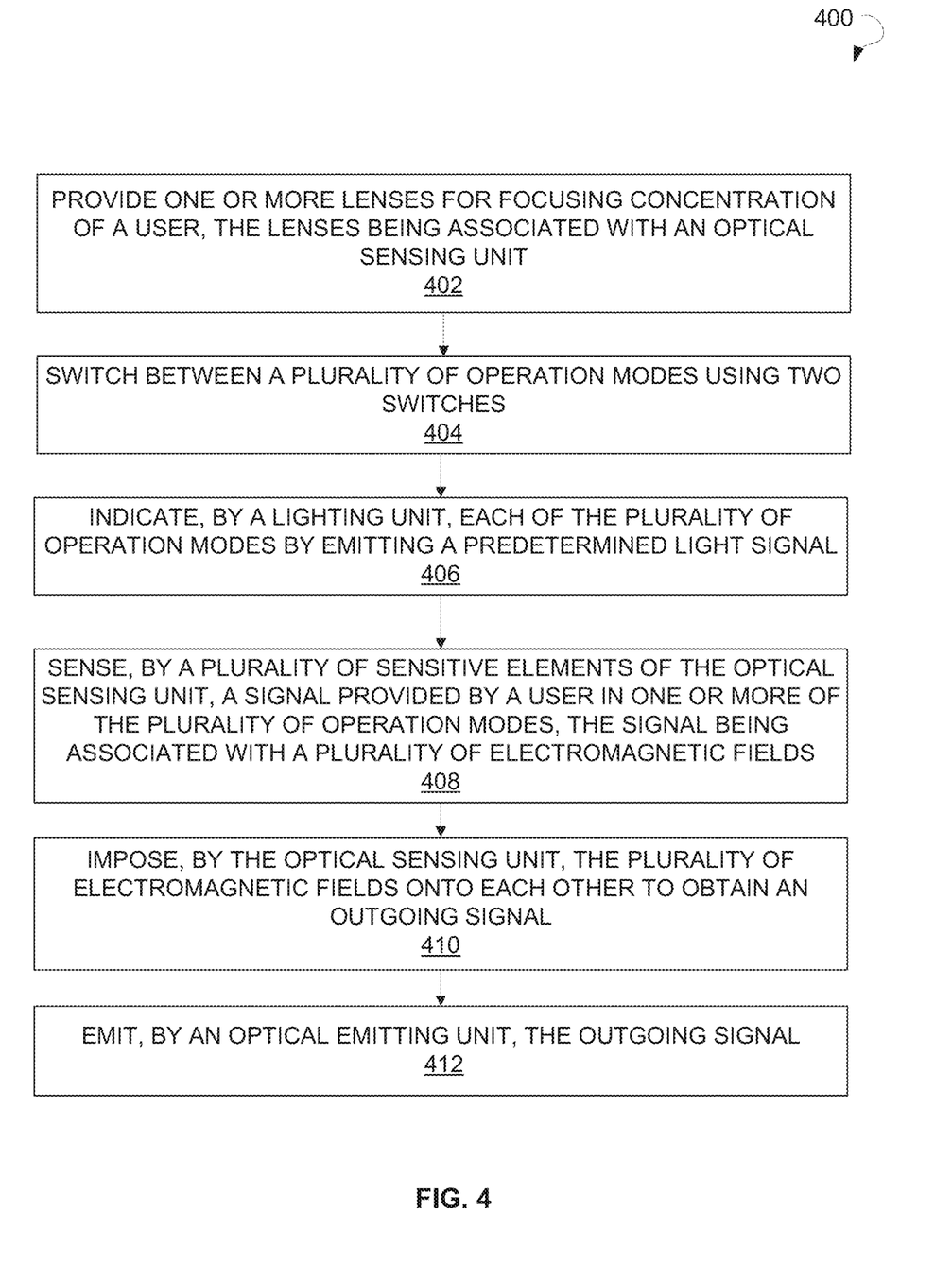
FIG. 4 is a flow chart illustrating a method for development of concentration, in accordance with an example embodiment.

FIG. 4 is a process flow diagram showing a method 400 for development of concentration, according to an example embodiment. In some embodiments, the operations may be combined, performed in parallel, or performed in a different order. The method 400 may also include additional or fewer operations than those illustrated.

The method 400 may commence with providing one or more lenses for focusing concentration of a user at operation 402. The lenses may be associated with an optical sensing unit. The method 400 may continue with switching between a plurality of operation modes using two switches at operation 404. Operation 406 of the method 400 may include indicating, by a lighting unit, each of the plurality of operation modes by emitting a predetermined light signal.

The method 400 may further include sensing, by a plurality of sensitive elements of the optical sensing unit, in one or more of the plurality of operation modes, a signal provided by the user at operation 408. The signal may be associated with a plurality of electromagnetic fields. The plurality of sensitive elements may be spherical. The signal provided by the user may be a biological signal.

The method 400 may further include imposing, based on the signal, by the optical sensing unit, the plurality of electromagnetic fields onto each other to obtain an outgoing signal at operation 410. Specifically, the method 400 may be performed by using signal conditioning by imposing electromagnetic fields resulting from the generation of a biological signal to each other. The method 400 may be performed in accordance with the principle of universal connection with control of the purpose of concentration, which can be developed according to techniques described by the inventor in the publications mentioned herein.

The method 400 may further include emitting, by an optical emitting unit, the outgoing signal at operation 412. The optical emitting unit may include an optical lens. The optical emitting unit may emit the outgoing signal in the form of at least an optical signal. The method 400 may further include converting, by a converting unit, the outgoing signal into an electrical signal.

In an example embodiment, the method 400 may further include providing a power source. The power source may be in communication with the optical sensing unit and the optical emitting unit. In an example embodiment, the method 400 may further include providing a housing and a cover. The one or more lenses may be disposed on the cover.

Figure 5A:
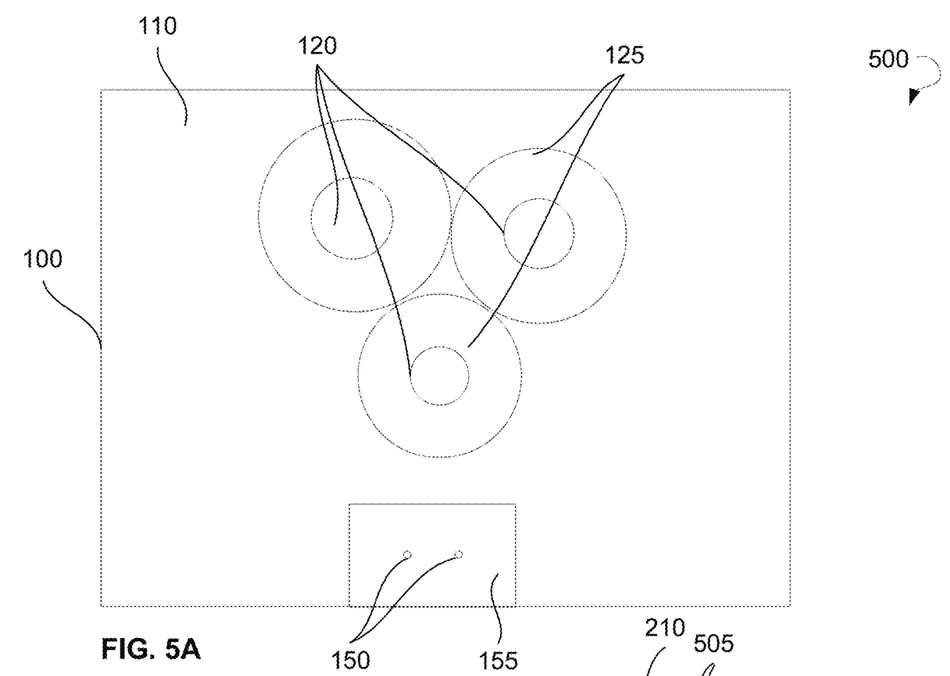
FIG. 5A is a schematic diagram illustrating a top view of a three-mode device for development of concentration when a cover is in a closed state, according to an example embodiment.

FIG. 5A shows a top view 500 of a device 100 when a cover 100 is in a closed state, according to an example embodiment. The device 100 may have three plates 125 on which lenses 120 may be fastened. The plates 125 may be attached to the cover 120. The device 100 may further have a plate 155 for fastening stones 150, such as crystals or diamonds. The plate 155 may be attached to the cover 110.

Figure 5B:
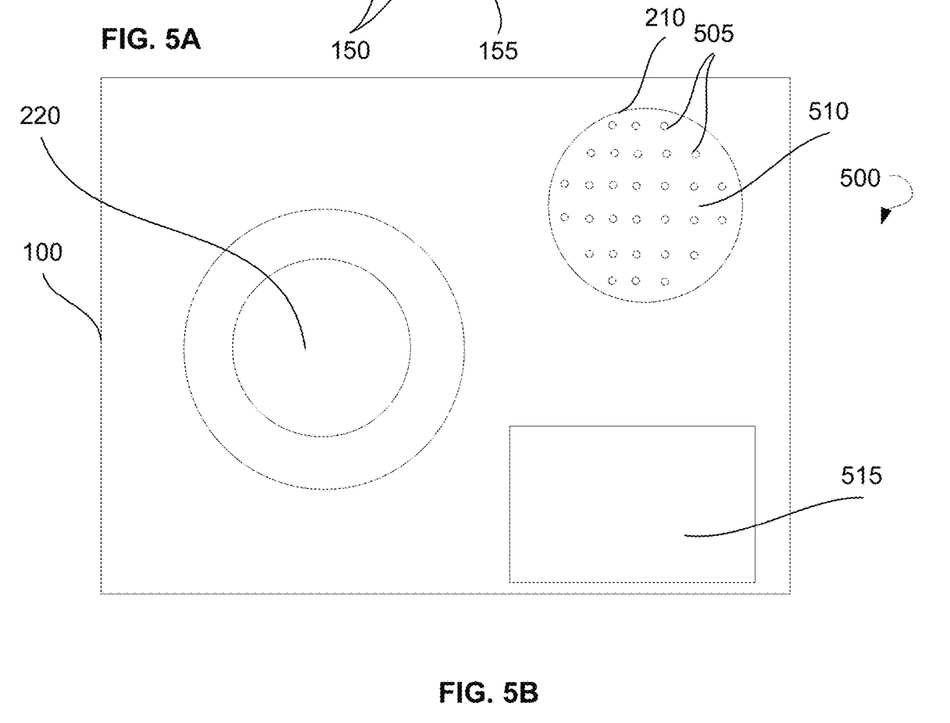
FIG. 5B is a schematic diagram illustrating a top view of a three-mode device for development of concentration when a cover is in an open state, according to an example embodiment.

FIG. 5B shows a top view 500 of the device 100 when the cover 100 is in an open state, according to an example embodiment. The device 100 may include an optical sensing unit 210, a plurality of sensitive elements 505, an optical emitting unit 220, a LED 510, and a converter 515. The plurality of sensitive elements 505 of the optical sensing unit 210 may sense the signal emitted by the user and provide the signal to the converter 515. The converter 515 may convert the signal into an electrical signal. The converter 515 may provide the electrical signal to the LED 510. The LED 510 may be electrically connected in parallel with other components of the device 100. Upon receipt of the electrical signal, the LED 510 may emit the electrical signal in the form of a light signal according to a current operation mode of the device 100.

The signal sensed by the plurality of sensitive elements 505 may be associated with a plurality of electromagnetic fields. The optical sensing unit 210 may impose the plurality of electromagnetic fields onto each other to obtain an outgoing signal. The optical sensing unit 210 may provide the outgoing signal to the optical emitting unit 220 for further emission of the outgoing signal by the optical emitting unit 220.

Figure 6A:
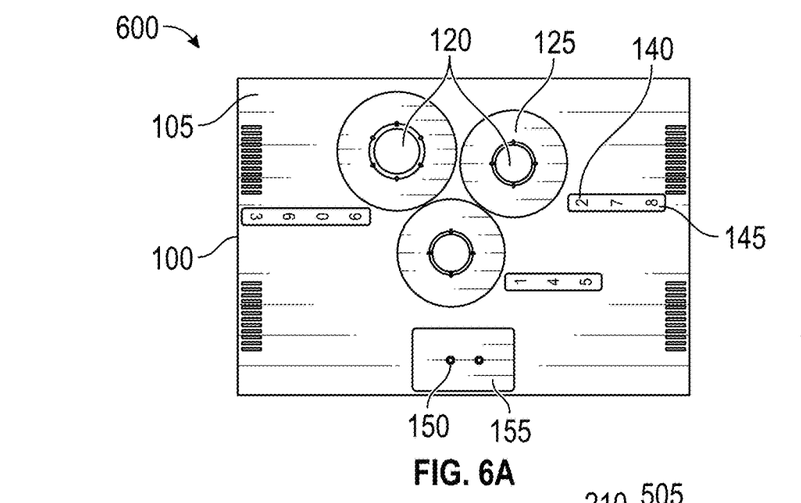
FIG. 6A shows a top view of a three-mode device for development of concentration when a cover is in a closed state, according to an example embodiment

FIG. 6A shows a top view 600 of the device 100 when the cover is in a closed state, according to an example embodiment. The device 100 may have three plates 125 onto which lenses 120 may be fastened. The plates 125 may be attached to the cover. The device 100 may further have a plate 155 for fastening stones 150, such as crystals or diamonds. The plate 155 may be attached to the cover. The device 100 may have one or more plates 140 with numerical symbols 145 depicted on the plates 140.

In a further example embodiment, the device 100 may have concentration enhancement elements. The concentration enhancement elements may be used for enhancing and accelerating the development of concentration. The concentration enhancement elements may include crystals and stones 150, e.g., diamonds or rock crystals.

Figure 6B:
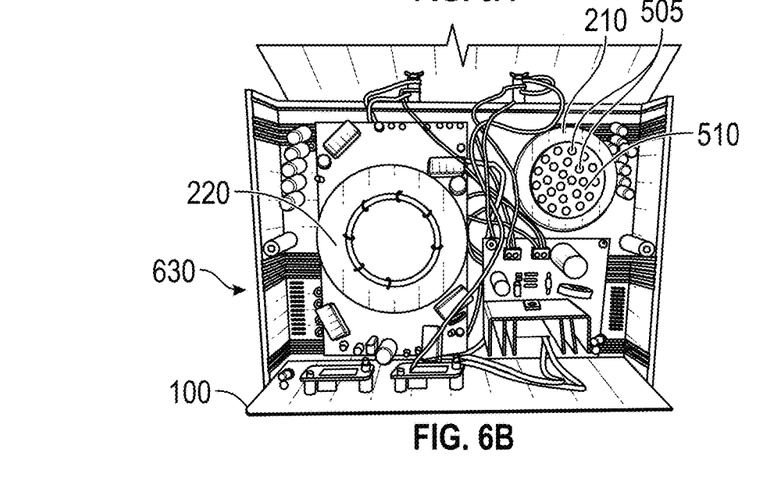
FIG. 6B shows a top view of a three-mode device for development of concentration when a cover is in an open state, according to an example embodiment.

FIG. 6B shows a top view 630 of the device 100 when the cover is in an open state, according to an example embodiment. The device 100 may include an optical sensing unit 210, a plurality of sensitive elements 505, an optical emitting unit 220, and a LED 510.

Figure 6C:
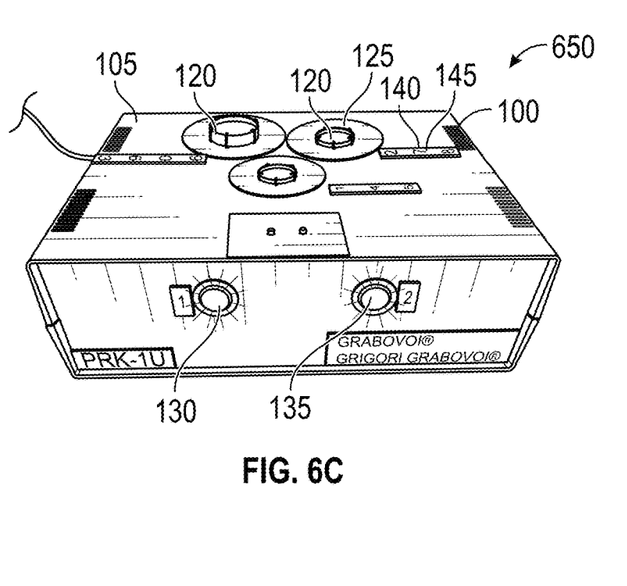
FIG. 6C shows a general perspective view of a three-mode device for development of concentration, according to an example embodiment.

FIG. 6C further shows a general perspective view 650 of the device 100, according to an example embodiment. The device 100 may include a first switch 130 and a second switch 135. The first switch 130 and the second switch 135 may be made of a transparent material, such as glass or plastic. When the LED 510 emits light inside the device 100, the light emitted from inside of the device 100 can be seen through the first switch 130 and the second switch 135.

In an example embodiment, figures may be placed on the cover in the form of numerical values 145. For example, figures 1, 4, 5 may be placed (e.g., written) near a smaller lens, and figures 2, 7, 8, and 9, 0, 6, 3 may be placed near larger lenses. The development of concentration using the presence of figures near the lenses can be made by concentrating on the lenses in a way described above and adding concentration on the figures.

Figure 7A:
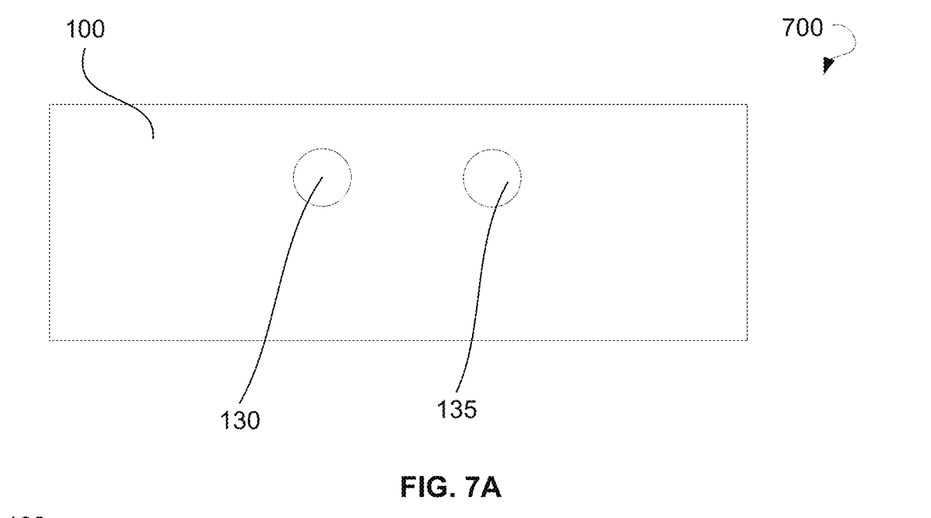
FIG. 7A shows a front view of a three-mode device for development of concentration, according to an example embodiment.

FIG. 7A shows a front view 700 of the device 100, according to an example embodiment. The device 100 may have a first switch 130 and a second switch 135. Each of the first switch 130 and the second switch 135 may be configured to operate in several positions. Specifically, the first switch 130 may be moved into an upward position to switch to a first operation mode. The second switch 135 may be moved into an upward position to switch to a second operation mode. The first switch 130 may be moved into a downward position and further moved into the upward position to switch a third operation mode.

Figure 7B:
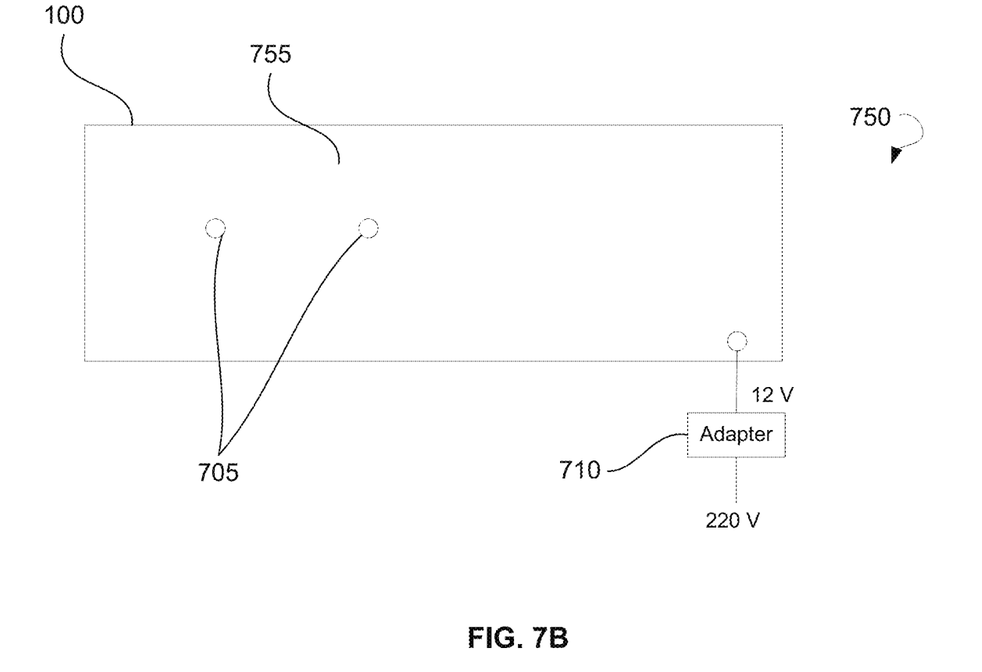
FIG. 7B is a rear view of a three-mode device for development of concentration, according to an example embodiment.

FIG. 7B shows a rear view 750 of the device 100, according to an example embodiment. The device 100 may have controlling elements 705 disposed in adjustment holes in the housing of the device 100 for tuning components of the device 100 using a side panel 755. The device 100 may be in communication with an adapter 710. The adapter 710 may be configured to convert the voltage of 220 V from a power grid into the voltage of 12 V consumed by the device 100.

Figure 8:
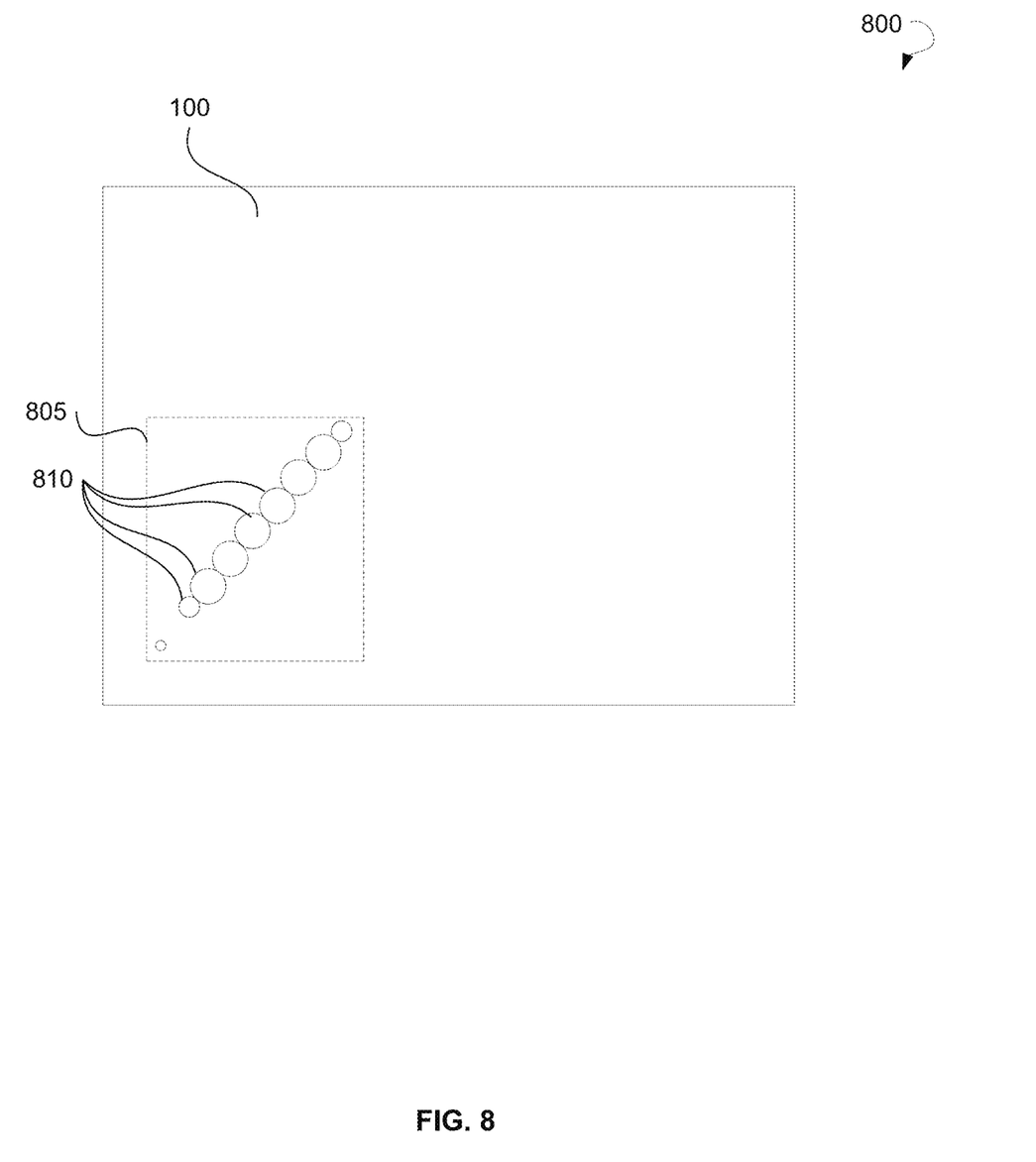
FIG. 8 shows a top view of a three-mode device for development of concentration, according to an example embodiment.

FIG. 8 shows a top view 800 of the device 100, according to an example embodiment. The device 100 may further include one or more crystal systems 805. The crystal system 805 may consist of a plurality of crystals 810. The crystals 810 may be used for focusing the concentration of the user. The crystal system 805 may be a vertical crystal system in which the crystals 810 may have different radii and, hence, different heights. The radius of the crystals 810 may be 7 mm, 12 mm, and so forth.

In an example embodiment, the three-mode device for development of concentration may be used remotely through video monitoring of the device by a user, including via the Internet. The three-mode device for development of concentration is applicable in various areas related to providing eternal life, such as becoming healthy, developing the quality of control forecasting or control foresight, rejuvenating an organism, and so forth.

Figure 9:
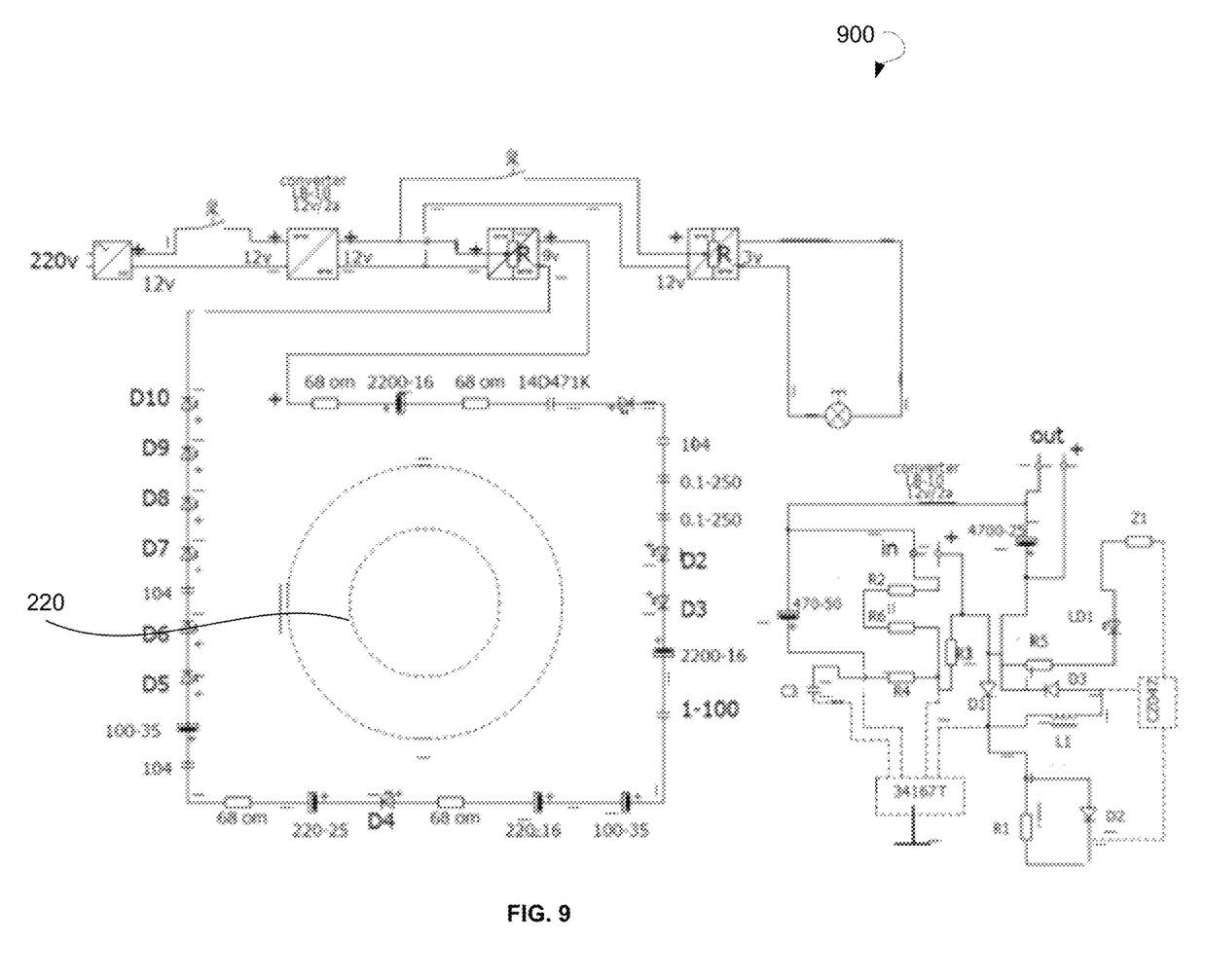
FIG. 9 is a schematic illustration showing elements of a three-mode device for development of concentration, according to an example embodiment.

FIG. 9 is a schematic diagram 900 illustrating a three-mode device for development of concentration, according to an example embodiment. The elements shown on FIG. 9 may be located inside a housing of the three-mode device for development of concentration. The three-mode device for development of concentration may include an optical emitting unit 220.

Example 1 of operation of a three-mode device for development of concentration. On day 1, a first user turned the three-mode device off and then turned on after some period of time. Upon being turned on, the three-mode device entered the first operation mode, in which a red light mostly did not light up, meaning that power provided to the diode was low. Upon switching the three-mode device manually to the second and third operation modes, the three-mode device did not react, i.e., did not switch to the second and third operation modes.

The three-mode device is configured for developing concentrations on eternal life. The three-mode device can switch to one of the operation modes upon increasing the control load. In view of this, four users started a concentration session using the three-mode device by concentrating on lenses for focusing concentration of the users.

Three days later, the three-mode device entered the second operation mode. The three-mode device worked stably, but the third mode could not be turned on. Four users continued performing concentration sessions during the next three days. The three-mode device was placed in a room of the first user during the time when the concentration sessions were performed.

After three days, the second user took the three-mode device to work in a room of the second user. The three-mode device was moved to the room and turned on. The second user continued performing the concentration session using the three-mode device by concentrating on lenses for focusing concentration of the users. Upon turning on, the three-mode device began to self-adjust as was seen from diode heating. In a few seconds, the three-mode device entered the third operation mode and began to work stably in all three operation modes.

After three hours of operation, the three-mode device was again transferred to a room of the first user and turned on. The first user continued performing the concentration session using the three-mode device by concentrating on lenses for focusing concentration of the users. Upon turning on, the three-mode device worked in the third operation mode. At the time of turning on of the three-mode device, the first user was located in proximity to the three-mode device and had a conversation and was distracted from the concentration session. In a several minutes, the three-mode device automatically switched to the second operation mode. When the third operation mode was manually turned on, the device did not respond. Then, the three-mode device was unplugged and moved to the room of the second user, where it worked steadily before. Upon being turned on, the three-mode device immediately entered the third operation mode and there were no failures in operation of the three-mode device The three-mode device worked stably in all three modes. After this check, the three-mode device was again transferred to the room of first user and turned on. The three-mode device did not work in the third operation mode in the room of the first user. Then, the operation of the three-mode device was re-tested in the room of the second user. The three-mode device was moved to the room of the second user and turned on. The three-mode device consistently entered all the three operation modes. The operation of the three-mode device was recorded by photographing the device. Each of the first user and the second user continued performing the concentration session using the three-mode device when the three-mode device was in the room of each of the users. Then, the three-mode device was turned off, moved again to the room of the first user, and turned on. The first user continued the concentration session by concentrating on lenses of the three-mode device. Upon turning on, the three-mode device entered all the three operation modes and began to work stably in all operation modes.

Thus, the three-mode device independently switches to one of the operation modes is response to the signals received from the users during the concentration sessions. This function of artificial intelligence of the three-mode device, i.e. automatic switching between the modes, is turning on in case of simultaneous receipt of an increased amount of signals, e.g., from several users.

Example 2 of operation of a three-mode device for development of concentration. A user travelled to a foreign country and had a 24 hours long layover between the flights. The user experienced strong emotions during the layover, such as intensive fear, worry, lack of self-confidence, and perplexity. The user arrived at the hotel during the layover, turned the three-mode device, and started a first concentration session by concentrating on lenses of the three-mode device. Upon switching on, the three-mode device operated in the third operation mode and did not respond to manual switching of the three-mode device by the user to the second operation mode or the first operation mode. The next day, the user had a flight to the foreign country and an emotional state of the user stabilized, i.e. the user had a normal emotional state. When the user arrived at the hotel, the user turned the three-mode device and started a second concentration session by concentrating on lenses of the three-mode device. Upon switching on, the three-mode device operated in the first operation mode. The user manually switched the three-mode device to the second operation mode and then to the third operation mode. The three-mode device responded to switching between the modes by the user and switched to the second operation mode or the third operation mode, respectively. It was concluded that the user had intensive emotions and thoughts during the first concentration session. In view of this, the intensity of a signal transmitted by the user to the three-mode device caused automatic switching of the three-mode device to the third operation mode, in which the three-mode device amplified the dynamic phase of reality.

Example 3 of operation of a three-mode device for development of concentration. A user conducted concentration sessions using the three-mode device for four days in a first city. The three-mode device operated properly and responded to switching between the operation modes by the user by operating in a first operation mode, a second operation mode, or the third operation mode, respectively. On day five, the user moved to a second city and, upon arrival, started a concentration session. The user turned the three-mode device on. The three-mode device operated in the first operation mode. The user attempted to manually switch the three-mode device to the second operation mode. In response to the attempt of the user, the three-mode device switched to the third operation mode and did not respond to further attempts of the user to switch the three-mode device to the second operation mode. The automatic switching of the three-mode device to the third operation mode continued in the course of concentration sessions conducted by the user during seven days. During this seven-day period, the user had intensive emotions and thoughts when conducting the concentration sessions. In view of this, the intensity of a signal transmitted by the user to the three-mode device caused automatic switching of the three-mode device to the third operation mode, in which the three-mode device amplified the dynamic phase of reality. After seven days, the emotional state of the user stabilized and the three-mode device started operating normally and responded to manual switching of the three-mode device by the user to the second operation mode or the third operation mode.

Figure 10:
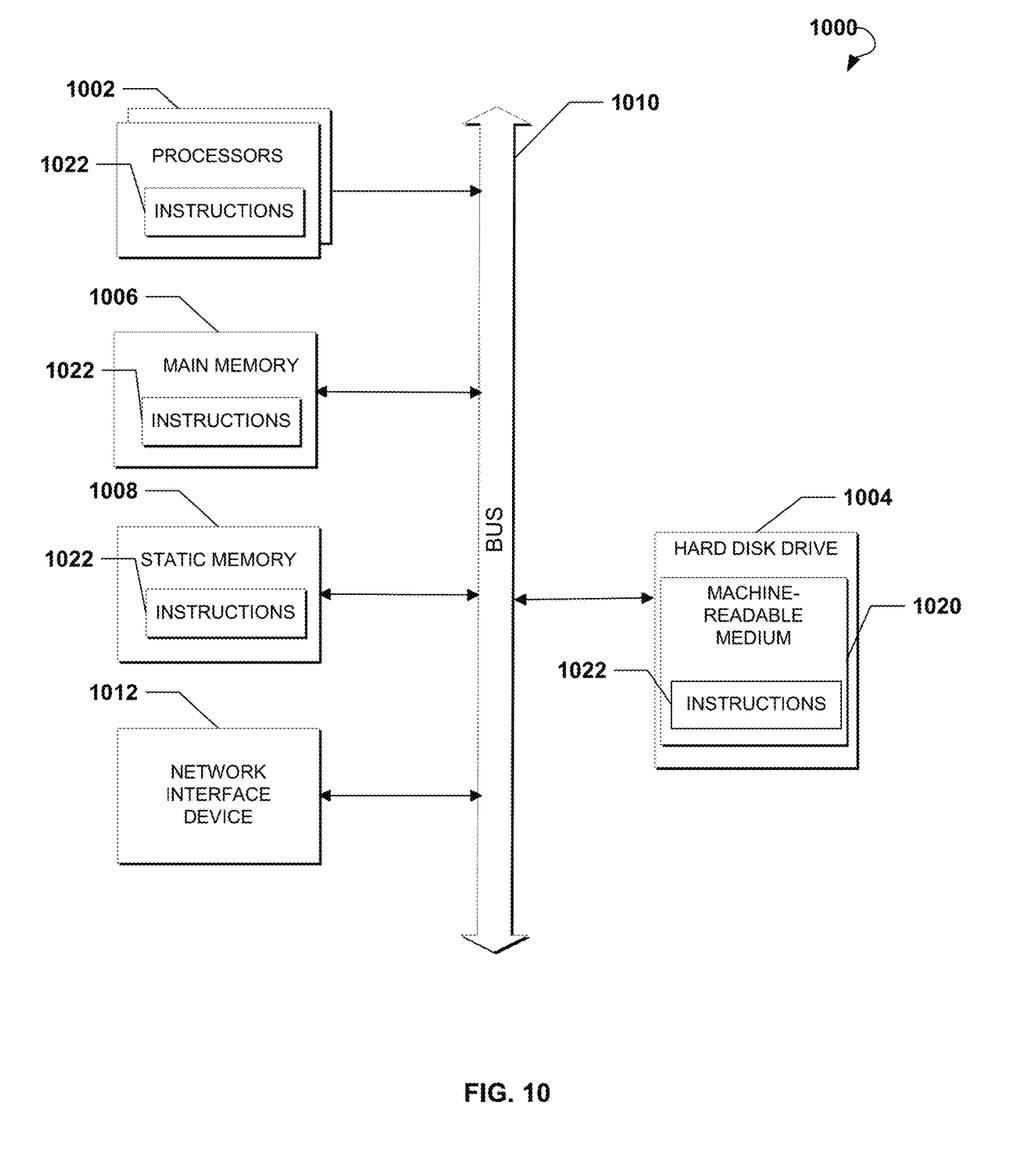
FIG. 10 shows a computing system that can be used to implement a method for development of concentration, according to an example embodiment.

FIG. 10 shows a diagrammatic representation of a computing device for a machine in the exemplary electronic form of a computer system 1000, within which a set of instructions for causing the machine to perform any one or more of the methodologies discussed herein can be executed. In various exemplary embodiments, the machine operates as a standalone device or can be connected (e.g., networked) to other machines. In a networked deployment, the machine can operate in the capacity of a server or a client machine in a server-client network environment, or as a peer machine in a peer-to-peer (or distributed) network environment. The machine can be a personal computer (PC), a tablet PC, a set-top box, a cellular telephone, a digital camera, a portable music player (e.g., a portable hard drive audio device, such as a Moving Picture Experts Group Audio Layer 3 (MP3) player), a web appliance, a network router, a switch, a bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The computer system 1000 may include a processor or multiple processors 1002, a hard disk drive 1004, a main memory 1006 and a static memory 1008, which communicate with each other via a bus 1010. The computer system 1000 may also include a network interface device 1012. The hard disk drive 1004 may include a computer-readable medium 1020, which stores one or more sets of instructions 1022 embodying or utilized by any one or more of the methodologies or functions described herein. The instructions 1022 can also reside, completely or at least partially, within the main memory 1006 and/or within the processors 1002 during execution thereof by the computer system 1000. The main memory 1006 and the processors 1002 also constitute machine-readable media.

While the computer-readable medium 1020 is shown in an exemplary embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media. Such media can also include, without limitation, hard disks, floppy disks, NAND or NOR flash memory, digital video disks, Random Access Memory, Read-Only Memory, and the like.

The example embodiments described herein may be implemented in an operating environment comprising software installed on a computer, in hardware, or in a combination of software and hardware.

Thus, three-mode devices and methods for development of concentration are described. Although embodiments have been described with reference to specific exemplary embodiments, it will be evident that various modifications and changes can be made to these exemplary embodiments without departing from the broader spirit and scope of the present application. Accordingly, the specification and drawings are to be regarded in an illustrative rather than a restrictive sense.

What is claimed is:

1. A three-mode device for development of concentration, the device comprising:
   a housing;
   a first optical unit disposed in the housing, the first optical unit comprising a plurality of spherical elements;
   a second optical unit disposed in the housing wherein the second optical unit includes an optical lens;
   one or more lenses for enabling a user to affix a user gaze on the one or more lenses;
   one or more plates attached to the housing, wherein the one or more lenses are placed on the one or more plates, wherein a diameter of the one or more plates exceeds a diameter of the one or more lenses;
   two switches for switching between a plurality of operation modes associated with emittance of a predetermined light signal, the two switches being disposed on the housing; and
   a lighting unit disposed in the housing and configured to indicate each of the plurality of operation modes by emitting the predetermined light signal.

2. The device of claim 1, further comprising a cover.

3. The device of claim 2, further comprising a plurality of figures placed on one of the housing and the cover, wherein the plurality of figures includes numerical symbols.

4. The device of claim 2, wherein the one or more lenses are disposed on the cover.

5. The device of claim 1, further comprising a power source in communication with the lighting unit.

6. The device of claim 1, wherein the plurality of operation modes includes:
   a first operation mode configured to be turned on by moving a first switch of the two switches into an upward position, the first operation mode being characterized by absence of emittance of a light signal by the lighting unit;
   a second operation mode configured to be turned on by moving a second switch of the two switches into an upward position, the second operation mode being characterized by emittance of a static light signal by the lighting unit; and
   a third operation mode configured to be turned on by moving the first switch into a downward position and further moving the first switch into the upward position, the third operation mode being characterized by emittance of a repetitively-pulsed light signal by the lighting unit.

7. The device of claim 1, wherein the plurality of spherical elements are made of glass.

8. The device of claim 1, wherein the optical lens is made of glass.

9. The device of claim 1, further comprising a further plurality of optical elements, wherein the further plurality of optical elements are selected from crystals and stones.

10. A method for development of concentration, the method comprising:
    providing a housing;

providing a first optical unit disposed in the housing, the first optical unit comprising a plurality of spherical elements;

providing a second optical unit disposed in the housing, wherein the second optical unit includes an optical lens;

providing one or more lenses for enabling a user to affix a user gaze on the one or more lenses;

providing one or more plates, wherein the one or more lenses are placed on the one or more plates, wherein a diameter of the one or more plates exceeds a diameter of the one or more lenses;

switching between a plurality of operation modes using two switches disposed on the housing, the plurality of operation modes being associated with emittance of a predetermined light signal; and indicating, by a lighting unit disposed in the housing, each of the plurality of operation modes by emitting the predetermined light signal.

11. The method of claim 10, further comprising providing a power source, wherein the power source is in communication with the lighting unit.

12. The method of claim 10, further comprising providing a cover.

13. The method of claim 12, further comprising providing a plurality of figures, wherein the plurality of figures includes numerical symbols placed on one of the housing and the cover.

14. The method of claim 12, wherein the one or more lenses are disposed on the cover.

15. A three-mode device for development of concentration, the device comprising:

a housing;

a first optical unit disposed in the housing, the first optical unit comprising a plurality of optical elements, wherein the plurality of optical elements are made of glass;

a second optical unit disposed in the housing, wherein the second optical unit includes an optical lens;

one or more lenses for enabling a user to affix a user gaze on the one or more lenses, the one or more lenses being made of glass;

one or more plates attached to the housing, wherein the one or more lenses are placed on the one or more plates, wherein a diameter of the one or more plates exceeds a diameter of the one or more lenses;

two switches for switching between a plurality of operation modes associated with emittance of a predetermined light signal, the two switches being disposed on the housing; and a lighting unit disposed in the housing and configured to indicate each of the plurality of operation modes by emitting the predetermined light signal, wherein the plurality of operation modes includes:

a first operation mode configured to be turned on by moving a first switch of the two switches into an upward position, the first operation mode being characterized by absence of emittance of a light signal by the lighting unit;

a second operation mode configured to be turned on by moving a second switch of the two switches into an upward position, the second operation mode being characterized by emittance of a static light signal by the lighting unit; and a third operation mode configured to be turned on by moving the first switch into a downward position and further moving the first switch into the upward position, the third operation mode being characterized by emittance of a repetitively-pulsed light signal by the lighting unit.

* * * * *